United States Patent [19]

Coy et al.

[11] Patent Number: 4,865,986

[45] Date of Patent: Sep. 12, 1989

[54] TEMPERATURE CONTROL APPARATUS

[75] Inventors: Richard A. Coy, Grass Lake; Roy A. Waycaster, Tecumseh, both of Mich.

[73] Assignee: Coy Corporation, Ann Arbor, Mich.

[21] Appl. No.: 254,255

[22] Filed: Oct. 6, 1988

[51] Int. Cl.[4] ........................ C12M 1/38; G01N 21/00

[52] U.S. Cl. .................................... 435/290; 435/286; 435/288; 435/296; 422/63

[58] Field of Search ............... 435/290, 300, 316, 286, 435/289, 288, 296; 422/67, 109, 173, 198, 202, 285, 290, 307

[56] References Cited

U.S. PATENT DOCUMENTS

| | | | |
|---|---|---|---|
| 3,106,010 | 10/1963 | Barnes | 435/300 X |
| 3,117,009 | 1/1964 | Boelter | 435/290 X |
| 4,195,131 | 3/1980 | Papas | 435/316 X |
| 4,252,897 | 2/1981 | Axford et al. | 435/289 X |
| 4,711,851 | 12/1987 | McNamara et al. | 435/290 X |

*Primary Examiner*—Larry Jones

*Attorney, Agent, or Firm*—Harness, Dickey & Pierce

[57] ABSTRACT

Apparatus is disclosed for controlling the heating and cooling of a plurality of upright containers containing a mixture used for performing gene amplification. The apparatus includes a support rack comprising aluminum blocks which is partially submerged in a thermally conductive fluid such that at least the lower portions of the containers are submerged in the fluid with the upper portions engaging the aluminum blocks for efficient heat transfer. Heaters are disposed within the aluminum block for heating the block and a plurality of thermoelectric cooling cells are used to cool the block. A programmable microprocessor is used for controlling the heating and cooling cycles, thereby allowing repetitive heating and cooling of the mixture to produce the copies of the genetic material sought to be copied. A cam separates the support rack from the cooling cells during the heating portion of the process.

10 Claims, 3 Drawing Sheets

TEMPERATURE CONTROL APPARATUS

BACKGROUND AND SUMMARY OF THE INVENTION

This invention relates to apparatus for providing precise temperature control to the heating and cooling cycles useful in many processes and particularly useful in the gene amplification process.

The gene amplification process uses an enzyme and its unqiue abilities to create a kind of chain reaction that duplicates a sample piece of genetic material, or DNA, with incredible rapidity. The process mixes together the enzyme, pieces of DNA building blocks known as nucleic acids, and a sample DNA molecule to be duplicated. The mix also includes specialized chemicals known as primers that can target a specific sample of the DNA to be multiplied. When the mix is heated, the enzyme goes to work, knitting together free building blocks to match the template provided by the sample DNA molecule. This mix is then cooled and the process is repeated.

When the original sample has been copied, the process is repeated and both the original and copied piece of DNA are then copied. After twenty cycles, approximately a million samples of the DNA molecule have been produced. This genetic material can then be easily analyzed by conventional methods. This process can reduce to hours a cloning procedure which previously required months to produce enough genetic material for analysis.

The process requires a heating phase and a cooling phase in each cycle. Once the mixture is heated to the desired temperature, it is held at this temperature for a period of time before cooling to a specified temperature at which the mixture is held again for a period of time.

To achieve the desired results, the heating must be performed uniformly and accurately. A rapid change in temperature during heating and cooling is desireable to reduce the time necessary for the process. It is necessary, however, to keep the temperature gradient across the mixture to no more than $\pm\frac{1}{2}°$ C. This small gradient is necessary to minimize variation in the gene amplification.

Accordingly it is an object of this invention to provide a device for accurately controlling the temperature of the mix during each cycle.

To accomplish this precise heating and cooling, the present invention utilizes a rack comprised of a plurality of aluminum blocks with vertical apertures therethrough for holding a plurality of upright containers such as test tubes. Heaters are sandwiched inbetween the aluminum blocks to heat the aluminum blocks. The rack is positioned within a fluid container which contains a quantity of a suitable thermally conductive fluid such as mineral oil, glycerine or the like. The fluid is in communication with each of the apertures and the lower portion of each upright container. The fluid container is positioned on an aluminum cooling block which rests upon a plurality of peltier cells for cooling the fluid container and rack during the cooling phase of the cycle.

The thermally conducting fluid and the aluminum blocks serve as a heating medium for the transfer of heat from the heaters to the upright containers. By using aluminum and a thermally conductive fluid which are efficient transfers of heat, the containers can be quickly and uniformly heated and cooled.

An electric gear motor is used to separate the fluid container from the cooling block during the heating phase of the cycle. This is necessary to prevent damage to the peltier cells by the heat. In addition, this allows for more rapid heating by eliminating the mass of the cooling block from the mass to be heated.

Further objects, features and advantages of the invention will become apparent from a consideration of the following description and the appended claims when taken in connection with the accompanying drawings.

DETAILED DESCRIPTION OF THE INVENTION

Figure 1:
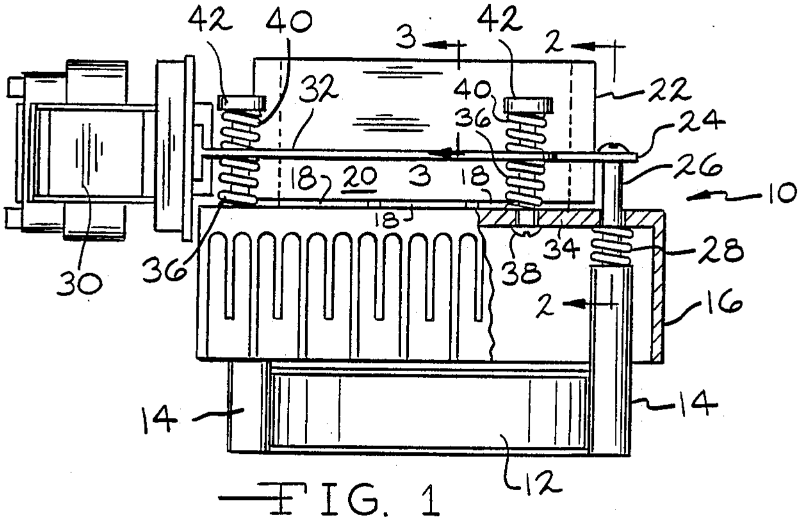
FIG. 1 is an elevational view of the temperature control apparatus of this invention.

Referring now to FIG. 1, the temperature control apparatus of this invention is shown generally at 10. Apparatus 10 includes a cooling fan 12 at the base. Support columns 14 are attached to the side of the fan 12 and extend upwardly therefrom. A heat sink 16 is supported upon the support columns 14. Heat sink 16 includes a flat upper plate 34 and a number of downwardly extending fins 35.

Resting on top of the upper plate 34 are a number of thermoelectric peltier cells 18 used to cool the DNA mixture. Cooling block 20 rests upon the peltier cells 18. Fluid container 22 in turn rests upon the top of the cooling block 20.

The fluid container 22 has four outwardly extending mounting bosses 24 extending from opposite sides of the container 22. The mounting bosses 24 are secured to the support columns 14 by screws 26 extending through apertures in the upper plate of the heat sink. A spring 28 is positioned between the top of the support columns 14 and the upper plate 34 of the heat sink. This allows for movement of the heat sink 16 downward as will be described below. The cooling block 20 and the peltier cells 18 are sandwiched between the upper plate 34 of the heat sink and the container 22.

An electric gear motor is mounted at one side of the container 22 by two elongated mounting bosses 32. Mounting bosses 32 are supported upon coil springs 36 surrounding screws 38 extending upward through upper plate 34. Coil springs 40 surround the screws 38 between the mounting bosses 32 and nuts 42 threaded to the end of the screws 38. The springs 36 and 40 are used to provide a floating mount for the electric gear motor 30 as will be described below.

Figure 2:
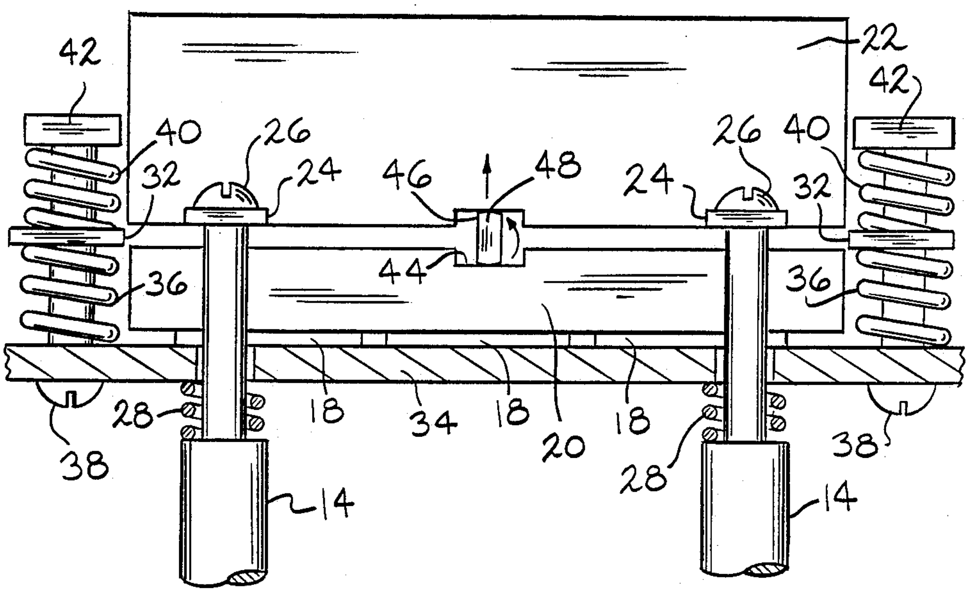
FIG. 2 is a cross sectional view as seen from substantially the line 2—2 of FIG. 1.

Referring now to FIG. 2, grooves 44 and 46 are shown in the upper surface of the cooling block 20 and lower surface of the fluid container 22 respectively. An elongated flat plate cam 48 is positioned within the grooves 44 and 46. The cam 48 is rotated by the electric gear motor 30 to separate the container 22 from the surface of the cooling block 20. In the position shown in FIG. 2, the cam 48 is in the vertical position in which it separates the container from the cooling block. When the cam 48 is in the horizontal position, the container bottom surface is engaging the upper surface of the cooling block for maximum heat transfer.

When the cam 48 is rotated to the vertical position, the cooling block 20 and the heat sink 16 are urged downward, compressing the coil springs 28. When the heat sink moves downward, the screws 38 also move downward resulting in compression of coil springs 40 and expansion of oil springs 36. The fluid container 22 remains substantially stationary. Therefore it is necessary to provide the electric motor and cam with a floating mount.

Figure 3:
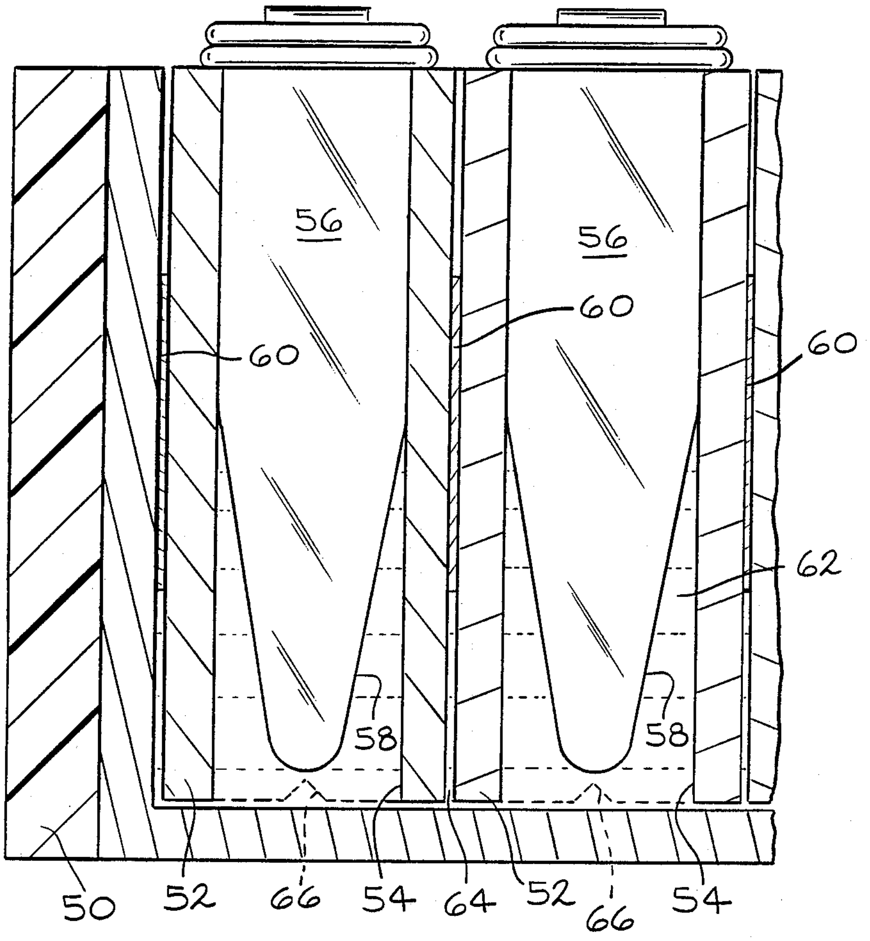
FIG. 3 is a cross sectional view as seen from substantially the line 3—3 of FIG. 1.

FIG. 3 is a cross sectional view of the container 22 showing the support rack and upright containers, in this case test tubes, therein. A layer of insulation 50 is provided around the sides of the container 22. The support rack consists of a plurality of rectangular aluminum blocks 52. Each block 52 has a single row of vertical apertures 54 machined through the block 52. Each aperture 54 is of the appropriate size for receiving and holding a test tube 56. The test tubes 56 have a substantially cylindrical upper portion and an inwardly tapered closed bottom portion 58. The apertures 54 are of a size to provide a snug fit for the cylindrical upper portion of the test tubes to maximize heat transfer between the test tubes and aluminum blocks.

Spaced longitudinally between the aluminum blocks 52 and the outer side of the end blocks 52 are resistance foil heaters 60. Heaters 60 are used to heat the test tubes and their contents.

The container 22 is filled with a predetermined amount of a thermally conductive fluid 62 such as mineral oil, glycerine or the like; the more thermally conductive the fluid the faster the response of the apparatus 10. In a commerical form of the invention mineral oil is used as the fluid 62 and it is satisfactory. When test tubes are inserted into the support rack, the fluid 62 occupies the space around the tapered portion 58 of the test tube as well as the space 64 between each blocks 52 below the foil heater 60. A small groove 66 is machined in the bottom of the blocks 52 so that the fluid in each aperture is in communication with the fluid in the other apertures 54. In this manner, the outer surface of the test tubes is in contact with either the thermally conductive fluid in the container 22 or the side wall of the apertures 54 such that uniform heating of the test tube and its contents can occur.

Figure 4:
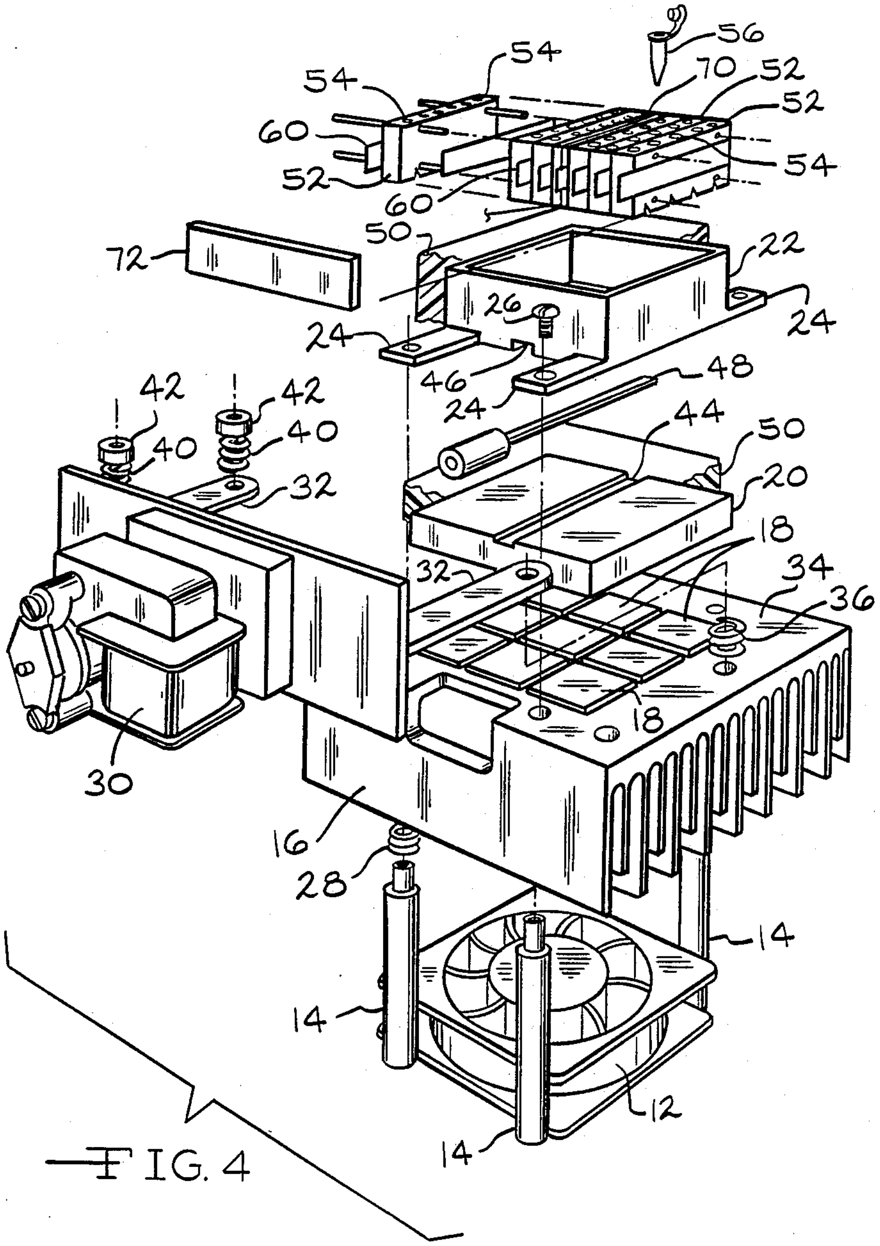
FIG. 4 is an exploded perspective view of the temperature control apparatus of this invention.

FIG. 4 shows an exploded perspective view of the entire assembly. The support rack is shown comprised of six aluminum blocks 52 which are held together by guide rods 68 extending through the blocks between apertures 54. The heaters 60 are sandwiched between each block and on the outside of the two end blocks. The heaters extend beyond the support rack on one side and connect with a printed circuit board 72. A thermocouple 70 is disposed within the support rack and is also connected with the circuit board 72. Thermocouple 70 is monitoring the temperature of the support rack.

A programmable microprocessor is used to control the heating and cooling of the support rack as well as the hold time at each temperature. The maximum rate of change of temperature is ½° C. per second for both the cooling and heating cycles. The temperature range of the apparatus is 0° to 105° C.

During cooling, the bottom surface of the container 22 engages the top surface of the cooling block 20. During heating, the electric motor 30 rotates cam 48 to separate the container 22 from the cooling block 20. This is accomplished by the cooling block and heat sink being moved downward. By separating the fluid container 22 and the cooling block 20, heating of the test tubes can proceed quicker by reducing the mass to be heated. In addition, this reduces the likelihood of damage to the peltier cells by overheating.

To perform gene amplification, the mixture, including the sample DNA to be copied, is placed in several upright container such as test tubes. The upright containers are then inserted into the aluminum block support rack in the container 22. The upper cylindrical portions of the upright containers are in contact with the aperture wall of the aluminum block. The lower tapered portions of the upright containers are in contact with the thermally conductive fluid 62.

The heaters are used to quickly heat the aluminum support rack and the fluid and thereby heat the upright containers and their contents to the desired temperature. The peltier cells are then used to cool the support rack and the fluid and thereby cool the upright containers and their contents. This process is then repeated several times until the desired number of copies of the target DNA sample have been reproduced.

It is to be understood that the invention is not limited to the exact construction or method illustrated and described above, but that various changes and modifications may be made without departing from the spirit and scope of the invention as defined in the following claims.

What is claimed is:

1. Apparatus for selectively heating and cooling a plurality of upright containers and their contents comprising:

a metal heating block with vertical cavities therethrough for supporting said upright containers;

a container for holding a quantity of thermally conductive fluid and for reception of said heating block within said fluid container with a portion of said upright containers in contact with the fluid;

means for heating the metal heating block and the fluid, said heating means being disposed within said heating block between said vertical cavities;

a metal cooling block below the fluid container and in vertical surface to surface engagement with said fluid container;

thermoelectric cooling means beneath said cooling block and engaging said cooling block for cooling said heating block and fluid;

temperature monitoring means within said heating block; and means selectively operative to provide alternatively for vertical separation of the fluid container and cooling block and vertical surface to surface engagement to enable heating of the contents of the upright containers rapidly and cooling of the contents of the upright containers rapidly while maintaining precise temperature conditions for precise periods of time.

2. The apparatus of claim 1 wherein said selectively operable means includes an electric motor.

3. The apparatus of claim 2 wherein said selectively operable means includes cam means disposed between said fluid container and said cooling block, said cam means rotatable from an engagement position wherein said fluid container and cooling block are in surface to surface engagement to a separation position wherein said cam means separates said fluid container from said cooling block, said cam means being rotatable by said electric motor.

4. The apparatus of claim 3 wherein said cam means includes an elongated flat plate having a greater width than thickness, said plate extending between the fluid container and cooling block and positioned within a longitudinal groove in the top of said cooling block and bottom of said fluid container.

5. The apparatus of claim 2 wherein said selectively operable means includes floating mount means for attaching said electric motor and cam means.

6. The apparatus of claim 1 wherein said heating means includes an electrical resistance heater.

7. The apparatus of claim 1 wherein said thermoelectric cooling means includes peltier cells.

8. The apparatus of claim 1 further comprising control means for selectively activating said heating and cooling means.

9. An apparatus for selectively heating and cooling a plurality of upright containers and the contents thereof, comprising:

a support rack having a plurality of metal blocks in a side-by-side relationship, each of said blocks having a plurality of vertical apertures therethrough for supporting said upright containers;

a container for holding a quantity of thermally conductive fluid for submerging a portion of said upright containers therein by placing said rack in said fluid container;

electric resistance heaters disposed between said metal blocks and engaging said blocks for heating said support rack and fluid and thereby heating said upright container;

a cooling block beneath said fluid container, said cooling block engageble with the bottom of said container;

a plurality of thermoelectric cooling cells beneath said cooling block and engaging said cooling block for cooling said cooling block, fluid container, support rack and fluid, thereby cooling said upright containers;

a thermocouple disposed within said support rack for monitoring the temperature of said rack;

control means for activating the heaters and cooling cells for alternating heating and cooling said upright containers; and means operatively associated with said fluid container and cooling block for selectively disengaging and engaging said fluid container and said cooling block.

10. The apparatus of claim 9 wherein said disengaging and engaging means includes cam means disposed between said fluid container and said cooling block, said cam means rotatable from an engagement position wherein said fluid container and cooling block are in surface to surface engagement to a separation position wherein said cam means separates said fluid container from said cooling block.

* * * * *